United States Patent [19]
McWilliams

[11] Patent Number: 5,788,674
[45] Date of Patent: Aug. 4, 1998

[54] APPARATUS AND METHOD FOR LIMITING FREE-FLOW IN AN INFUSION SYSTEM

[75] Inventor: Mark D. McWilliams, San Diego, Calif.

[73] Assignee: Medication Delivery Devices, Inc., San Diego, Calif.

[21] Appl. No.: 611,274

[22] Filed: Mar. 5, 1996

[51] Int. Cl.$^6$ .................................................. A61M 31/00
[52] U.S. Cl. .................................. 604/141; 604/67
[58] Field of Search ............................ 604/131, 118, 604/246, 403, 905, 280, 283, 151, 141, 65, 67

[56] References Cited

U.S. PATENT DOCUMENTS

| | | | |
|---|---|---|---|
| 3,868,973 | 3/1975 | Bierman | 604/246 |
| 3,890,968 | 6/1975 | Pierce | 604/65 |
| 3,901,231 | 8/1975 | Olson | 604/65 |
| 4,038,982 | 8/1977 | Burke | 604/65 |
| 4,121,584 | 10/1978 | Turner | 604/246 |
| 4,262,824 | 4/1981 | Hrynewycz | 604/246 |
| 4,585,441 | 4/1986 | Archibald | 604/65 |
| 4,913,703 | 4/1990 | Pasqualucci | 604/151 |
| 5,211,626 | 5/1993 | Frank | 604/65 |
| 5,257,978 | 11/1993 | Haber | 604/250 |
| 5,308,335 | 5/1994 | Ross et al. | 604/141 |
| 5,419,770 | 5/1995 | Crass | 604/123 |
| 5,437,635 | 8/1995 | Fields | 604/65 |
| 5,531,697 | 7/1996 | Olsen | 604/151 |
| 5,531,698 | 7/1996 | Olsen | 604/131 |

FOREIGN PATENT DOCUMENTS

0346548   12/1989   European Pat. Off. ............. 604/151

*Primary Examiner*—Michael A. Brown
*Attorney, Agent, or Firm*—Fish & Richardson P.C.

[57] ABSTRACT

A detachable apparatus for limiting the rate at which a fluid is supplied to a patient by a positive pressure infusion device. The infusion device has an operating device pressure of at least approximately 2 psi. The apparatus includes a constrained flow segment (or CFS), coupleable to and detachable from the infusion device, for delivering fluid to the patient from the infusion device. The CFS has a length, an inside diameter, and a hydraulic resistance. The hydraulic resistance is a function of the length and inside diameter. When the apparatus is not in a free-flow condition, the CFS delivers fluid to the patient at a controlled flow rate determined by the operating device pressure and the hydraulic resistance of the CFS. When the apparatus is in a free-flow condition, the hydraulic resistance of the CFS limits a maximum flow rate of the apparatus to less than about 50% of the controlled flow rate. An adaptor is also provided for enabling a non-activating intravascular set ("IV set") to be used with an infusion device designed to be used only with an activating IV set. The infusion device has a detector element for detecting whether an IV set being used with the infusion device is an activating IV set. The infusion device is activated in response to detection of an activating IV set and is disabled if no such IV set is detected. The adaptor comprises an active element, independent of an IV set, for interacting with the detector element. The active element causes the detector element to detect the presence of an activating IV set when, in reality, a non-activating IV set is being used.

32 Claims, 6 Drawing Sheets

APPARATUS AND METHOD FOR LIMITING FREE-FLOW IN AN INFUSION SYSTEM

BACKGROUND OF THE INVENTION

1. Field of the Invention

The present invention relates generally to infusion systems used in medical applications. More particularly, the present invention relates to an apparatus and method for limiting the flow of fluid being delivered by an infusion system, such as an infusion pump system, when the system is in a free-flow condition and for adapting the infusion system for use with many types of intravascular fluid reservoirs.

2. Description of Related Art

Intravascular administration sets that are useful for infusing medical treatment solutions and fluids to a patient are well known and widely used. In the most simple configuration, the intravascular fluid administration set includes a fluid source, an intravascular line connecting the fluid source to the patient, and a device operatively associated with the intravascular line to influence the rate of fluid flow to the patient. Flow rate control devices may be characterized as either positive pressure devices or controllers. Controllers rely on gravity for the flow of treatment fluid through the system, while positive pressure devices exert a force on the fluid to establish a fluid flow. Positive pressure devices include pumps, which exert an electromechanical force, and elastomeric fluid bags, in which the bag exerts a compressive force on the fluid based on the elastic property of the bag.

Pumps are often preferred because they can deliver higher pressures and can accurately deliver a wide range of flow rates. Pumps have some inherent disadvantages, however, that render them less than ideal, e.g., cost, complexity, size, and general lack of mobility. There is, therefore, a need for pumps that are relatively small and simple to operate, yet that are relatively accurate and reliable (and that preferably utilize a minimum number of components in the fluid containment and delivery set thereof). The ability to produce a pump that is portable and relatively inexpensive to manufacture would be beneficial in the field of medical treatment fluid delivery, especially in the home care setting. This need has been met in the form of the portable pump disclosed in U.S. Pat. No. 5,308,335, entitled "Infusion Pump, Treatment Fluid Bag Therefor, and Method for the Use Thereof," issued May 3, 1994, which is hereby incorporated by this reference.

In some intravascular administration sets, the intravascular line comprises a segment that can constrain the flow of fluid to the patient and that can be detached from the positive-pressure device. (For the remainder of this description, such a segment will be referred to as a "constrained flow segment" or "CFS." The CFS may comprise the entire coupling between the fluid reservoir (or fluid bag) and the patient, or may comprise a portion of that coupling.) A detachable CFS provides the advantages of being not only replaceable when it wears out or malfunctions, but also interchangeable to suit different conditions resulting from, for example, the administration of different fluids. Administration sets that utilize non-detachable CFS's do not provide these significant advantages.

Conventional positive-pressure systems incorporating detachable constrained flow segments suffer from a significant disadvantage, in that when a malfunction or disturbance occurs so as to allow a free-flow of fluid in the CFS, the rate of fluid flow is nearly the same as when the system is in a non-free-flow (or normal) condition. In a positive-pressure system, in the non-free-flow condition, fluid is delivered at a flow rate determined by the operating pressure of the positive-pressure device (i.e., the pump or elastomeric bag). In conventional positive-pressure systems, when some event occurs that causes the system to enter a free-flow condition, the fluid will continue to be delivered generally at a much greater flow rate than in the non-free-flow condition. Thus, the free-flow rate is generally much greater than the normal operating flow rate. As a result, a substantial amount of fluid may be delivered to the patient when the system is in free-flow, thus presenting a possible medical problem.

Some prior art infusion systems are designed such that they can be used only with a custom (or activating) fluid reservoir and CFS. (For the remainder of the description, "intravascular set" or "IV set" will be used to refer to a device that comprises the fluid reservoir and CFS.) Such activating IV sets are equipped with an activator element that interacts with a detector element present in the infusion device. The presence of the activator element indicates to the infusion device (via the detector) the presence of an activating IV set, thereby rendering the infusion device operable. Standard (or non-activating) IV sets, however, are not equipped with such an activator element. Accordingly, if one attempts to use a non-activating IV set in an infusion device equipped with a detector element, the infusion device will be disabled due to the absence of an activation element.

It may be advantageous in some cases to be able to use a standard, non-activating IV set with an infusion device that is designed for use only with activating IV sets. For example, standard IV sets may be more cost effective and/or more readily obtainable than activating IV sets, or the activating IV sets may be in short supply, while standard IV sets are plentiful.

Therefore, a need exists for an apparatus for limiting the rate of fluid flow when a positive pressure infusion system is in a free-flow condition, and that enables use of standard, non-activating IV sets in infusion devices designed only to be used with activating IV sets. The present invention provides such apparatus.

SUMMARY OF THE INVETION

Accordingly, the present invention is an apparatus for limiting or controlling the rate of fluid flow in a positive-pressure infusion system when the system is in a free-flow condition. The apparatus and method of the present invention can be used to limit free-flow in any type of positive-pressure infusion system, including infusion pumps and elastomeric fluid bags. Moreover, the present invention includes an adaptor for enabling the use of a standard, non-activating IV set with an infusion device designed only for use with activating IV sets.

In a first aspect, the present invention is a detachable apparatus for limiting the rate at which a fluid or solution is supplied to a patient by a positive-pressure infusion device, such as a pump or elastomeric fluid bag, having an operating device pressure of at least about 2 psi. The detachable apparatus includes a constrained flow segment (or CFS) that is coupleable to and detachable from the infusion device. The CFS has a length, inside diameter, and hydraulic resistance. The hydraulic resistance is a function of the length and inside diameter of the CFS. The CFS is designed to deliver fluid to a patient from the infusion device. When the detachable apparatus is not in a free-flow condition, the CFS delivers fluid to the patient at a controlled flow rate determined by the operating device pressure and the hydraulic resistance of the CFS. When the detachable apparatus is in a free-flow condition, the hydraulic resistance limits a maximum flow rate of the apparatus to less than about 50% of the controlled flow rate.

The CFS preferably includes a relatively long piece of tubing, having a length between about 30 and 76 inches, and a connector for connecting (directly or indirectly) to a patient. Preferably, the inside diameter of the tubing is substantially uniform from the infision device to the connector. This provides the advantages of ease of manufacturing, low cost, and adaptability.

As a function of the length and diameter of the tubing, the CFS has a maximum gravity pressure. The maximum gravity pressure is the pressure exerted on the CFS when it is full of fluid and suspended from an end such that the CFS hangs from the suspension point and the fluid in the tubing is completely under the force of gravity. In the preferred embodiment, the hydraulic resistance of the CFS is selected to limit the pressure exerted on the CFS to about the maximum gravity pressure when the positive-pressure infusion device is in a free-flow condition. As a consequence, the free-flow rate will be a relatively small fraction of the controlled flow rate of the CFS. Preferably, this fractional free-flow rate is less than about 50% of the controlled flow rate.

In another aspect, the present invention is a method for limiting the rate at which a fluid is supplied to a patient by a positive pressure infusion device having an operating device pressure of at least approximately 2 psi. The method comprises coupling a detachable apparatus to the infusion device. The apparatus includes a CFS having a length, an inside diameter, and a hydraulic resistance, where the hydraulic resistance is a function of the length and inside diameter. The method further comprises delivering fluid via the CFS from the infision device to the patient, such that: (1) when the apparatus is not in a free-flow condition, fluid is delivered to the patient at a controlled flow rate determined by the operating device pressure and the hydraulic resistance; and (2) when the apparatus is in a free-flow condition, the hydraulic resistance limits a maximum flow rate of the apparatus to less than about 50% of the controlled flow rate.

In yet another aspect, the present invention includes an adaptor for enabling use of a standard, non-activating IV set with an infusion device that is configured for use only with an activating IV set. Some infusion devices are equipped with a detector element for detecting the presence of an activating IV set fitted with a device that interacts with the detector and indicates that an activating IV set is being used. Non-activating IV sets, on the other hand, have no such interacting device. If an activating IV set is detected, the infusion device is enabled and thus rendered operable. In the absence of an activating IV set, the infusion device is disabled.

The adaptor of the present invention can be used to activate an infusion device equipped with a detector element when a non-activating IV set is positioned in the infusion device. The adaptor is positioned relative to the detector element of the infusion device, indicating the presence of an activating IV set. The infusion device is then enabled, despite the absence of an activating IV set.

The adaptor of the present invention preferably includes a casing and an active element. The casing is formed such that it holds the active element and allows it to interact with the detector element. Preferably, the casing has a recess formed in it that accepts the active element and has a covering portion that is bonded over the recess and active element to secure the active element within the casing.

The novel features of this invention, as well as the invention itself, both as to its structure and its operation, will be further understood from the accompanying drawings, taken in conjunction with the accompanying description.

BRIEF DESCRIPTION OF THE DRAWINGS

FIG. 4a and 4b illustrate two embodiments of the activator means employed in conjunction with the fluid treatment bag of the present invention.

Like reference numbers and designations in the various drawings indicate like elements.

DETAILED DESCRIPTION OF THE INVENTION

Throughout this description, the preferred embodiment and examples shown should be considered as exemplars, rather than as limitations on the present invention.

OVERVIEW

Fluid pumps can be used to infuse intravascular treatment fluid to a patient. One type of prior art infusion pump comprises: a collapsible treatment fluid bag; an inflatable bladder juxtaposed with the treatment fluid bag; means to vent the bladder; means for impinging the bladder against the treatment fluid bag as the bladder is inflated: a control assembly for controllably inflating the bladder to collapse the treatment fluid bag and expel treatment fluid from the bag; and a constrained flow segment (CFS) in fluid communication with the treatment fluid bag and the patient.

In accordance with the present invention, the CFS is designed such that it acts to limit the flow rate of fluid when the CFS is in a free-flow condition. Free-flow may be caused by a malfunction or disturbance in the pump, or by operator error. (Operator error generally occurs in the alternate-site environment, where unskilled persons may use the equipment.)

Treatment fluid bags contemplated for use in the above-described prior art infusion pump can be viewed as modified versions of conventionally available treatment fluid bags. One such modification is the presence of an activator capable of interacting with the control assembly of the pump, so as to enable the control assembly of the pump to operate. The control assembly is disabled in the absence of the activator means.

The presence of the activator ensures that the pump is operable for the delivery of treatment fluid to the patient only when an activating fluid bag containing the desired treatment fluid is inserted into the containment means of the pump. Thus, only the desired treatment fluid is delivered to the patient, and such treatment fluid is provided at an appropriate target flow rate. Disabling of the pump in the absence of an activating fluid bag prevents delivery of treatment fluids not contemplated for use with the particular configuration (i.e., flow rate, quantity of treatment fluid, etc.) of the pump.

Various types of activators may be employed. First, a mechanical activator may be used, which operates via a lock and key or mechanical switch. An alternative mechanical activator employs a special fluid bag configuration, so that only the appropriate bag size and configuration will fit in the containment means and thereby activate the pump. Second, the pump may include a magnetic activator. In this case, a magnet is positioned in the containment means and a piece of ferrite is positioned in the fluid bag, such that placing the bag in the containment means enables a control circuit. Third, the activator may comprise an electrical contact or circuit. Here, appropriate positioning of the fluid bag in the containment means completes a circuit and thereby enables the pump. Fourth, an optical coupling may be employed as an activator, so that the presence of the fluid bag in the containment means completes an optical circuit. Those skilled in the art will recognize that other, alternative activators can be used in the pump. Further description of suitable activators is provided below.

In addition to the activator, the CFS optionally further comprises a built-in flow restrictor; a fitment for attaching the treatment fluid bag to a needle or to a patient's catheter site; a clamp to stop the flow of the treatment fluid before, during, or after delivery of the treatment fluid to the patient; a filter in the tubing line; and the like. The CFS may also be coupled to an extension set, as will be described in greater detail below.

THE INFUSION PUMP AND FLUID BAG

Figure 1:
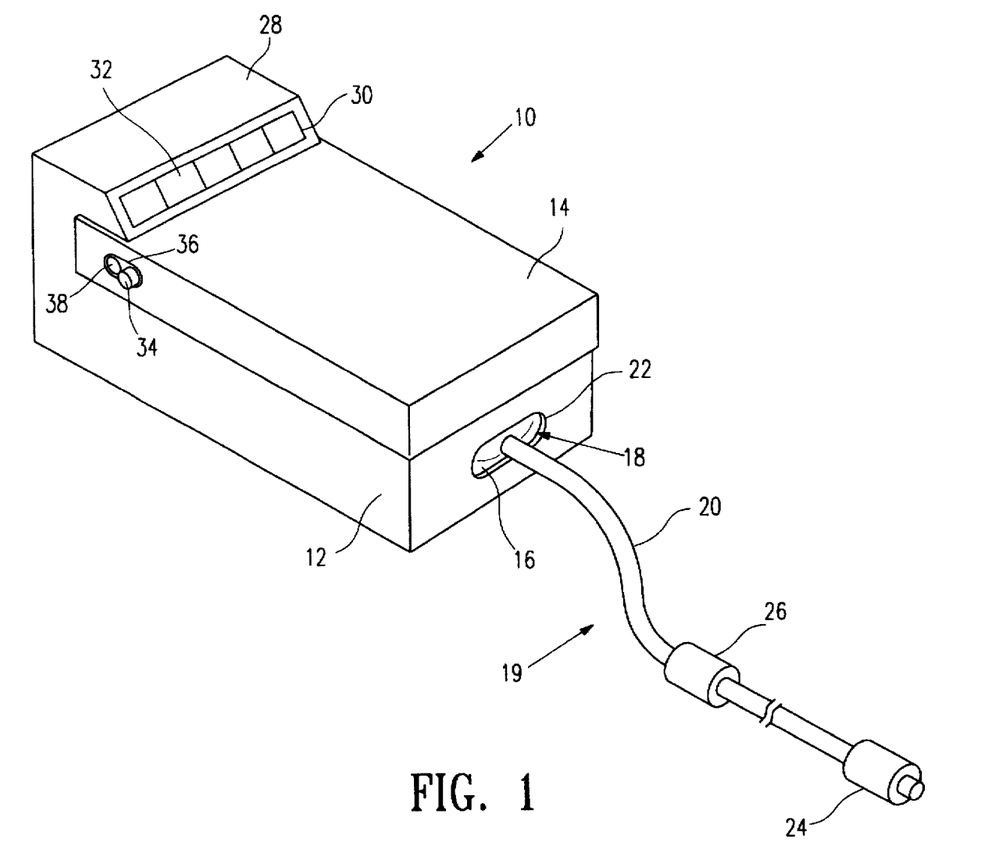
FIG. 1 is a perspective view of one embodiment of a prior art infusion pump.

FIG. 1 shows a first embodiment of a conventional infusion pump 10. Infusion pump 10 is housed within a pair of containment members. The lower containment member 12 is known as a base, and the upper containment member 14 is a cover plate, known as a platen. A prefilled collapsible treatment fluid bag 17 (shown in FIG. 2) is retained within a receptacle 16 formed by the base 12. A CFS 19, which includes a flexible outlet tube 20, extends from the bag 17 and exits receptacle 16 via an opening 22 in the base 12. Outlet tube 20 extends to a patient who is to be intravascularly infused. The CFS 19 also may include a site adaptor fitting 24, which is provided at the end of the tube 20. The site adaptor fitting 24 enables communication between the tube 20 and a vein of the patient.

Outlet tube 20 is preferably a conventional flexible plastic medical tubing having a predetermined fixed inner diameter. A flow restrictor 26, which is also part of the CFS 19, may optionally be positioned along tube 20. The flow restrictor 26 intervenes in the treatment fluid flowpath of tube 20 to further narrow the inner diameter of tube 20 as originally manufactured to a reduced fixed inner diameter.

A housing 28 for a control assembly can be provided on the pump 10. The control assembly may be positioned internal to the housing 28, as described below. The control assembly housing 28 may be integral with the base 12 and has an input station 30 on its face. The input station 30 may include a plurality of touch keys 32 for entering operational commands to the control assembly.

A latch 34 may be positioned on the cover plate 14. The latch 34 extends from a latch opening 36 in the plate 14. The latch 34 is provided for the locking cover plate 14 in place when it engages the base 12. A drive fluid vent 38 (formed in the base 12) may be positioned in alignment with the latch opening 36 and latch 34 when the cover plate 14 engages the base 12. The drive fluid vent 38 enables discharge of drive fluid from a drive fluid bladder, which is retained within the receptacle 16 when the latch 34 is in the unlocked position, as shown. Once the latch 34 is slid into the locked position over the vent 38, discharge of drive fluid is blocked.

The base 12 and cover plate 14 can be fixably engaged in a variety of ways, for example, by a combination of hinges and latches. The hinges and latches can be positioned on the front, side, or back of the base 12 and/or cover plate 14. Preferably, the hinges and latches are positioned on opposing sides of the base 12 and/or cover plate 14.

Figure 2:
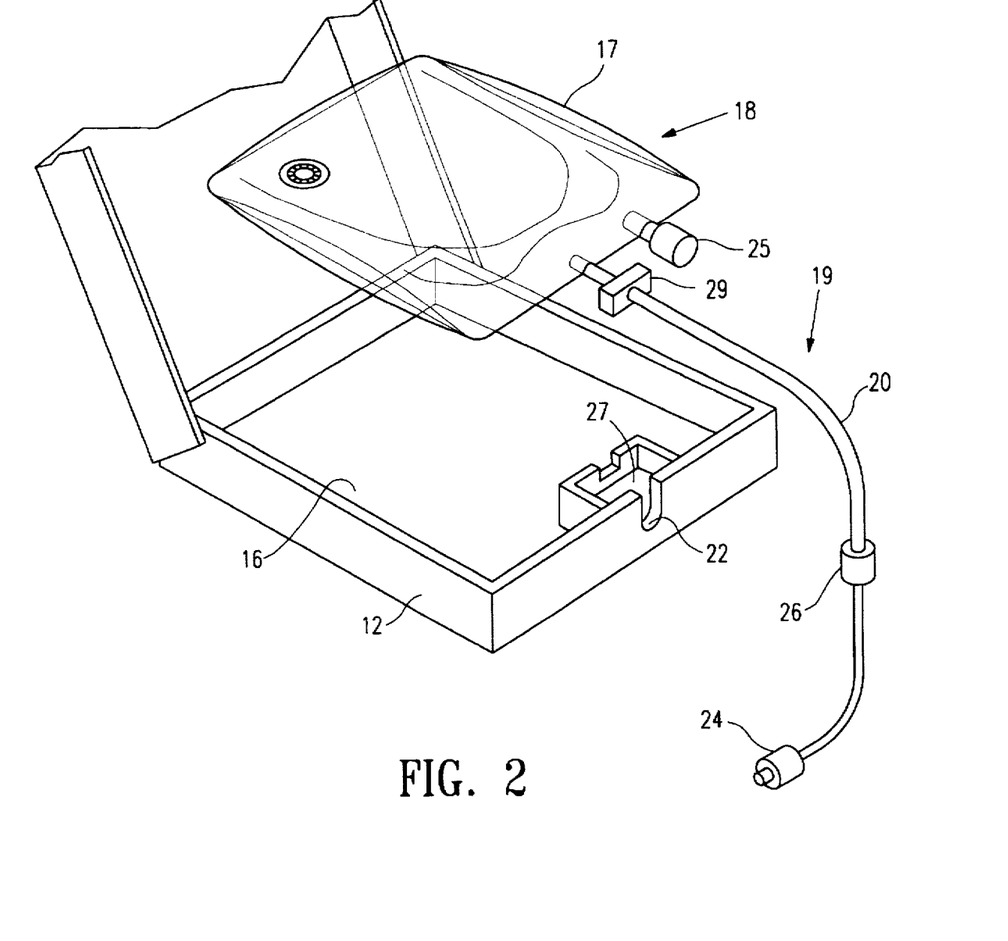
FIG. 2 is a schematic of a pump and treatment fluid reservoir with an activator device.

An exemplary treatment fluid bag 17 of the invention is shown in FIG. 2. The fluid bag 17 is retained in the base 12 of the pump 10. The base 12 forms a receptacle 16. The flexible outlet tube 20 passes through an opening 22 in the base 12. An optional flow restrictor 26, site adaptor fitting 24, and fill port/air vent 25 are also provided. The activator 29 is designed such that it can be placed with the containment means 27.

FREE-FLOW RATE LIMITER

Figure 3A:
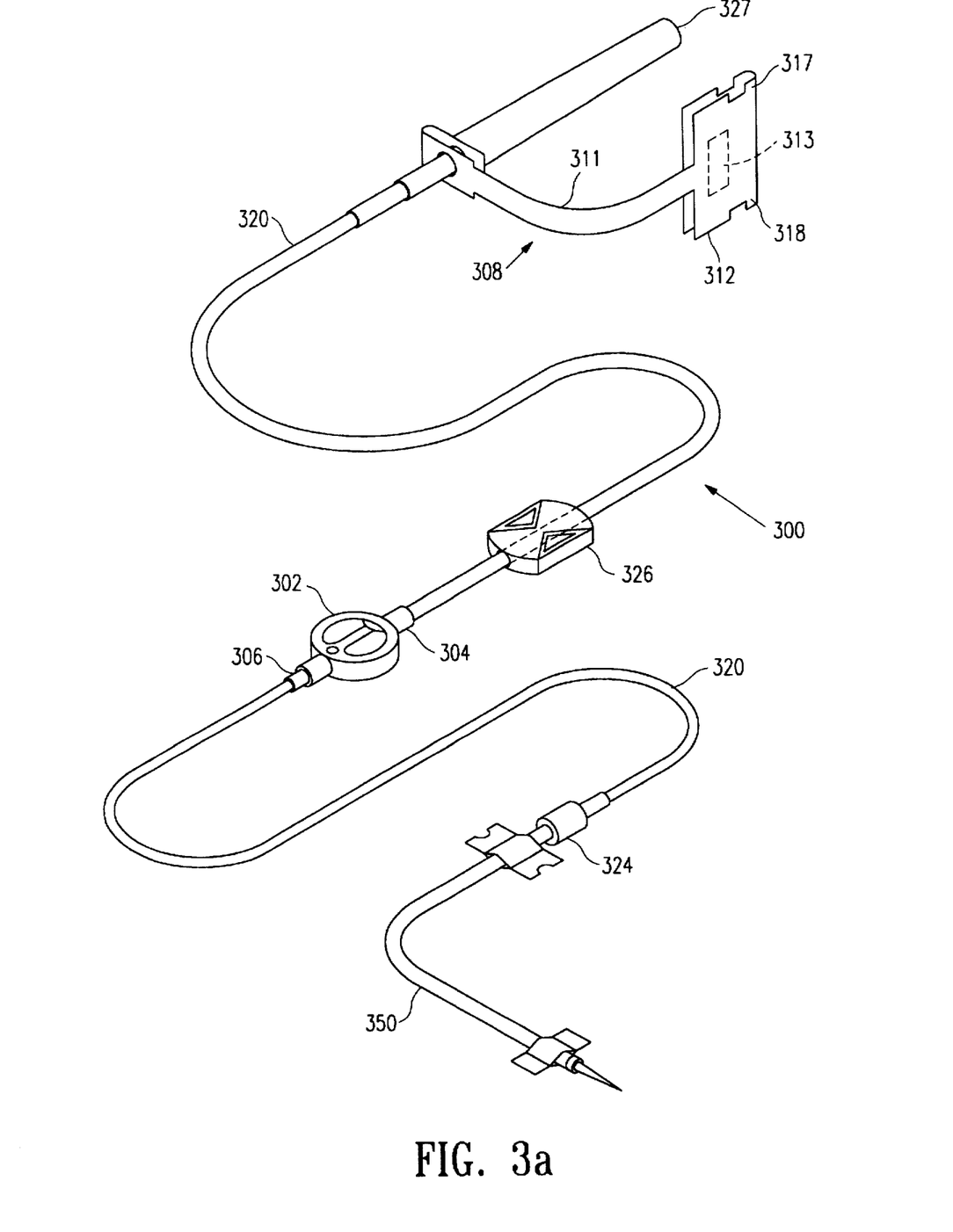
FIG. 3a is a perspective view of a constrained flow segment (CFS) for limiting the flow rate of fluid when the CFS is in a free-flow condition in accordance with the present invention. The CFS has an IV set adaptor in accordance with the present invention.

FIG. 3a shows a perspective view of a CFS 300 for limiting the flow rate of fluid when the CFS 300 is in a free-flow condition. The CFS 300 includes an infusion device connector 327 for connecting the CFS 300 to a positive pressure infusion device, such as pump 10. An outlet tube 320 extends from the connector 327 past an optional flow restrictor 326 to a first end 304 of an optional air/particle filter 302 for removing air that may be present in the outlet tube 320. Outlet tube 320 extends from a second end 306 of the air/particle remover 302 to a site adaptor fitting 324. An optional extension set 350 may be coupled to the CFS 300. The extension set 350 is used to extend the length of the intravenous line between the pump and the patient. Ideally, the extension set 350 does not constrain the fluid flow.

The outlet tube 320 preferably has a uniform inside diameter along its entire length. If an air particle filter 302 is included in the CFS 300, as shown in FIG. 3a, the inside diameter is preferably uniform on both parts of the outlet tube 320. This eliminates the need for manufacturing tubing of two different inside diameters. The length of the outlet tube 320 (not including fittings) is preferably in the range of 30" to 72", but those skilled in the art will recognize that the outlet tube 320 (and hence CFS 300) can have any reasonable length. Preferably, the inside diameter of the outlet tube 320 is in the range of 0.004 to 0.03 inch, depending on the length of the outlet tube 320 and on the operating pressure of the infusion system (e.g., pump) to which the outlet tube 320 is to be coupled. Again, those skilled in the art will recognize that this range for the inside diameter of the outlet tube 320 is not exclusive. Thus, an outlet tube 320 having a different diameter could alternatively be used.

The CFS 300 of the present invention provides a significant reduction in fluid flow rate when in a free-flow condition. Commonly, positive-pressure infusion devices have an operating device pressure in a range of about 2 psi to 12 psi. The operating pressure is the pressure level that will be exerted on a CFS when in a non-free-flow (or normal operating) condition. If the CFS is removed from the infusion device, filled with fluid, and suspended by one end, a "maximum gravity pressure" is the pressure exerted on the outlet tube 320 by the fluid as a result of the force of gravity exerted on the fluid. The maximum gravity pressure is dependent on the length of the tubing. As an example, the maximum gravity pressure of a fluid having a viscosity similar to water is as follows:

(1) Tubing length=30": Maximum gravity pressure=1.1 psi (2) Tubing length=72": Maximum gravity pressure=2.5 psi The following table (TABLE 1) is derived from the preceding relationships. TABLE 1 illustrates the reduction in flow rate that results if the CFS is designed for the operating device pressure and the CFS is exposed to the maximum gravity pressure.

TABLE 1

| Tubing Set Length | Maximum Gravity Pressure | Operating Device Pressure | |
|---|---|---|---|
| | | 5 psi | 12 psi |
| 36" | 1.30 psi | 26% | 11% |
| 72" | 2.5 psi | 50% | 21% |

For example, for tubing having a length of 36", the maximum gravity pressure is 1.30 psi. Accordingly, if the positive-pressure infusion device has an operating pressure of 5 psi, and the maximum gravity pressure is exerted on the CFS in free-flow, the flow rate in free-flow is only 26% of the flow rate in non-free-flow. Thus, it can be seen that a substantial reduction in flow rate results by designing the CFS such that the operating device pressure is substantially higher than the maximum gravity pressure exerted on the CFS when in a free-flow condition. Thus, an inherently safe medication delivery system can be designed, where the rate of medication delivered under free flow conditions is always less than under normal operating conditions.

The free-flow rate of a CFS is a function of the hydraulic resistance of the tubing. The hydraulic resistance is a function of the length and inside diameter of the tubing in the CFS. The greater the hydraulic resistance, the lower the flow rate, at a given pressure. Accordingly, if the tubing of the CFS is designed such that it has a high hydraulic resistance, the free-flow rate will be relatively small. The hydraulic resistance can be selected to specifically tailor the free-flow rate to a desired level. In accordance with the present invention, the desired level is the flow rate at maximum gravity pressure of the CFS.

The hydraulic resistance of the CFS tubing can be determined by the following relationships:

Equation 1: $R_H = P/Q$, where $R_H$ is the hydraulic resistance (in psi-hr/ml), P is the operating pressure of the infusion device (in psi), and Q is the free-flow rate of the infusion device (in ml/hr) at the operating pressure. For long tubes with small diameters, $R_H$ can be approximated as follows:

Equation 2: $R_H = C'(L/D^4)$, where C' is a constant for a particular fluid and temperature (here, $5.66 \times 10^{-6}$ for water at 72° F.); L is the length of the tubing; and D is the inside diameter of the tubing. Combining Equations 1 and 2, the following results:

Equation 3: $D^4/L = PC'/Q$

Solving for D, the following results:
Equation 4:

$$D = \sqrt[4]{PC'L/Q}$$

The following is a sample calculation for D, where L=36", P=5 psi, and Q=0.5 ml/hr:

$$D = \sqrt[4]{(5)(5.66 \times 10^{-6})(36)/(0.05)}$$

$$D = 0.00431 \text{ inch}$$

Thus, the inside diameter of the CFS tubing should be approximately 0.00431 inch so that the CFS, in a free-flow condition, will have the flow rate corresponding to the maximum gravity pressure of the CFS. The following table illustrates calculated exemplary inside diameters and hydraulic resistances for CFS's having tubing lengths of 36" and 72" and infusion devices having operating pressures of 5 psi and 12 psi:

TABLE 2

| FLOW RATE (ml/hr) | L = 36" PRESSURE | | L = 72" PRESSURE | |
|---|---|---|---|---|
| | 5 psi | 12 psi | 5 psi | 12 psi |
| 0.5 | $R_H = 10$ | $R_H = 24$ | $R_H = 10$ | $R_H = 24$ |
| | D = 0.00431 | D = 0.00346 | D = 0.005126 | D = 0.004119 |
| 5 | $R_H = 1$ | $R_H = 2.4$ | $R_H = 1$ | $R_H = 2.4$ |
| | D = 0.00776 | D = 0.00616 | D = 0.009136 | D = 0.007328 |
| 50 | $R_H = 0.1$ | $R_H = 0.24$ | $R_H = 0.1$ | $R_H = 0.24$ |
| | D = 0.01363 | D = 0.01096 | D = 0.01621 | D = 0.01303 |
| 500 | $R_H = 0.01$ | $R_H = 0.024$ | $R_H = 0.01$ | $R_H = 0.024$ |
| | D = 0.02424 | D = 0.01948 | D = 0.02883 | D = 0.02316 |

Therefore, in accordance with the above-described principles and interrelationships, the CFS 300 delivers fluid in a free-flow condition at a flow rate substantially less than the flow rate in a non-free-flow condition. Preferably, the infusion device used with the CFS 300 has an operating device pressure of at least approximately 2 psi, and the CFS 300 is coupleable to and detachable from the infusion device. When the CFS 300 is not in a free-flow condition, it delivers fluid to a patient at a controlled flow rate determined by the operating device pressure of the infusion device and the hydraulic resistance of the CFS 300. When the apparatus is in a free-flow condition, the hydraulic resistance of the CFS 300 limits its maximum flow rate to less than about 50% of the controlled flow rate.

FLUID BAG ACTIVATOR AND ADAPTOR

FIG. 2 shows a pump 10 that is designed to be used only with a special intravascular set (IV set) 18 (e.g., fluid bag 17 and CFS 19) customized for use with the particular pump 10. (Such custom IV sets will be referred to herein as "activating IV sets." It should also be understood, however, that the device that activates the pump may only comprise a fluid reservoir 17 and activator 19, as opposed to a fluid reservoir 17 and CFS 19. Thus, the CFS 19 may be a separate element.

In any case, the term IV set will be used for convenience herein and should not be construed as limiting on the present invention.) Pump 10 is equipped with a containment means 27, which includes a detector element (not shown), such as a magnetic or electrical switch or optical sensor, that prevents the pump 10 from being operated when an activating IV set 18 is not present. The activating IV set 18 includes an activator 29. The activator 29 fits into containment means 27 on the pump. When the activator 29 is properly inserted into containment means 27, the detector element detects the presence of the activator 29, and the pump 10 is enabled. If a standard fluid bag (ie., one without an activator) is used, the pump 10 fails to detect the presence of the activating IV set 18. As a result, the pump 10 is disabled.

Figure 4A:
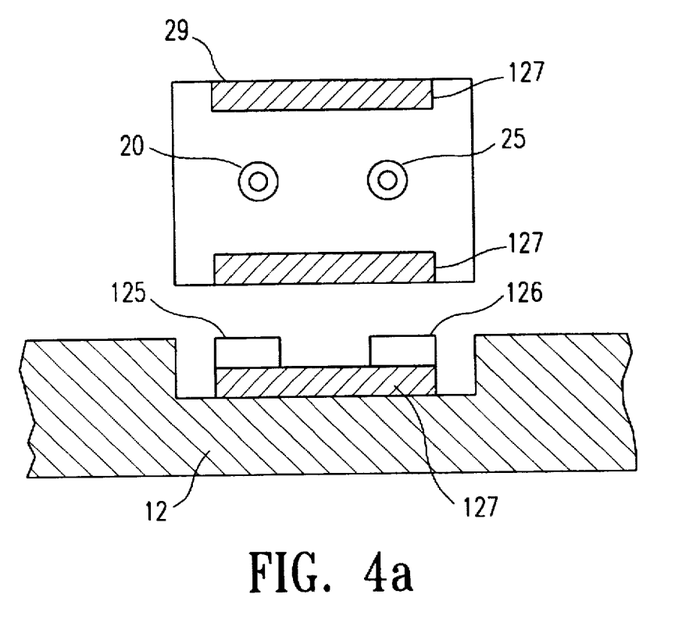
FIG. 4a illustrates an example construction employing a magnetically operated activator means wherein a Hall switch becomes actuated when the fluid treatment bag containing a soft iron bar therein is positioned within the containment means so as to complete the magnetic circuit.
Figure 4B:
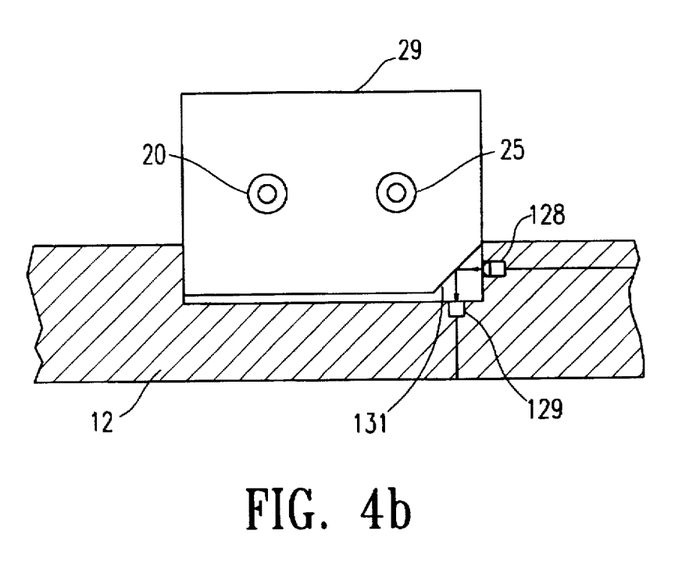
FIG. 4b illustrates an example of an optical activator means wherein light emitted from an LED is reflected onto a receiving detector by a surface associated with the fluid treatment bag, when the fluid treatment bag within the containment means of the invention pump. Thus, the presence of the reflective surface is indicative of the presence of the proper IV set (which includes the fluid bag) in the containment means.

FIGS. 4a and 4b illustrate two embodiments of an activator 29 that can be employed in conjunction with the IV set of the present invention. FIG. 4a shows a first embodiment of the activator 29, in which the detector comprises a Hall switch having contacts 125, 126. The activator 29 has at least one iron bar 127 that engages contacts 125, 126. As shown, the activator 29 may have iron bars 127 on both sides, so that one of the iron bars 127 will engage the contacts 125, 126 regardless of which side of the activator 29 is inserted into the containment means 27. When the activator 29 is properly positioned within the containment means 27, the iron bar 127 engages the contacts 125, 126, closing a circuit and thereby activating the pump 10. FIG. 4b shows an optical activator, in which the detector element comprises a LED 128 and receiving detector 129. When the activator 29 is properly positioned within the containment means 27, light is emitted from the LED 128 and is reflected onto the receiving detector 129 by a light reflecting surface 131 associated with the activator 29. The presence of the reflective surface 131 causes light to be received by the receiving detector 129 and indicates the presence of an activating IV set 18 within the pump 10. It may be desirable, however, to use a standard IV set (i.e., one without an activator) in a pump equipped with a Hall switch, optical activator, or other similar device for detecting the presence of an activating IV set. ("Standard" IV sets will be referred to as "non-activating IV sets.") Yet, if one attempts to use a non-activating IV set with such a pump, the pump will not work. Accordingly, it would be desirable to provide an IV set adaptor that would permit a non-activating IV set to be used with such a specialized pump, despite the absence of an activator on the IV set.

FIG. 3a shows an exemplary IV set adaptor 308 in accordance with the present invention. The IV set adaptor 308 can be inserted into containment means 27 in place of activator 29 in order to activate a pump. In consequence, a non-activating IV set can be used with a pump normally designed for use only with an IV set equipped with activator 29. As embodied herein, the adaptor 308 may include a tether 311 that permits the adaptor 308 to be attached to the CFS 300, preferably at or near connector 327. Those skilled in the art will recognize that attaching the adaptor 308 to the CFS 300 is merely a convenience. Thus, alternatively, the adaptor 308 could be an independent unit unattached to any other element, or the adaptor 308 could be attached to the pump 10. Moreover, although the adaptor 308 is described with reference to pump 10, it should be understood that the adaptor 308 could be used with any pump having a detector element that disables the pump unless an activating IV set is present.

Figure 3B:
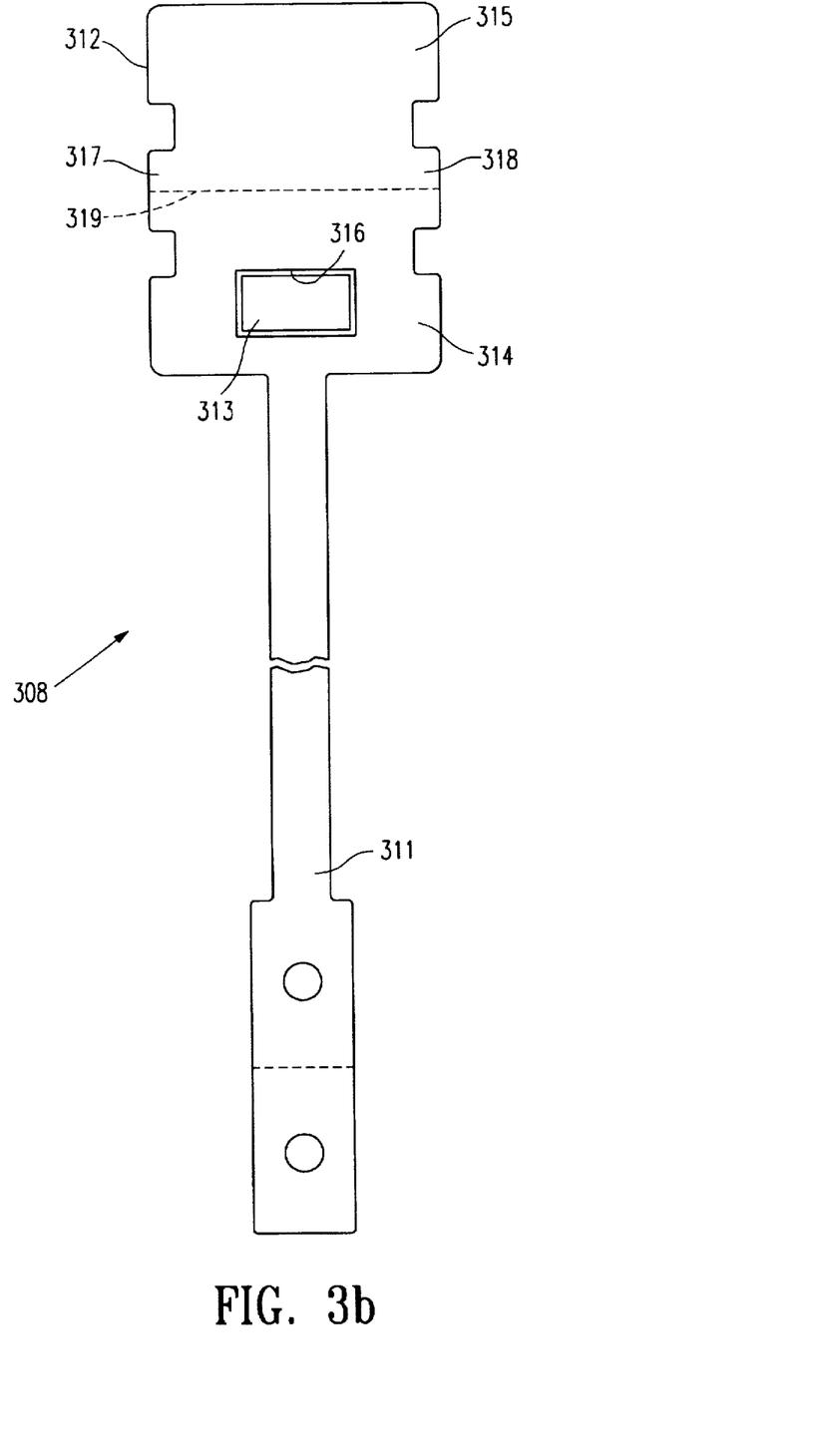
FIG. 3b is a top view of the IV set adaptor of the present invention.

FIG. 3b is a top view of the IV set adaptor 308. The adaptor 308 may include a holder means or casing 312 that holds an active element 313. The active element 313 indicates to the detector element (located within the containment means 27) the presence of an activating IV set, even when a non-activating IV set is being used. The casing 312 may be a one piece unit having two portions 314, 315. A recess 316 may be provided in one of the portions 314 that is designed to accept the active element 313. An adhesive may be applied to the second portion 315, which is folded over the first portion 314 along line 319, thereby covering the recess 316 and active element 313 and securing the active element 313 within the casing 312. The casing may have tabs 317, 318 (better shown in FIG. 3a) for securing the casing 312 within the containment means 27.

This casing configuration is merely exemplary, however, and it will be recognized that many other casing configurations may optionally be used. The specific configuration will depend, in part, on the type of detector element present in the containment means 27 and, in part, on the configuration of the containment means 27. Indeed, the active element 313 may be configured such that no casing 312 is required. In such a case, the active element 313 alone could be positioned within the containment means 27. The active element 313 may be, for example, a magnetic, electronic, or optical element, depending on the type of detector element present in the containment means 27. Those skilled in the art will recognize that other suitable activator and detector elements could be used in the present invention.

Figure 5:
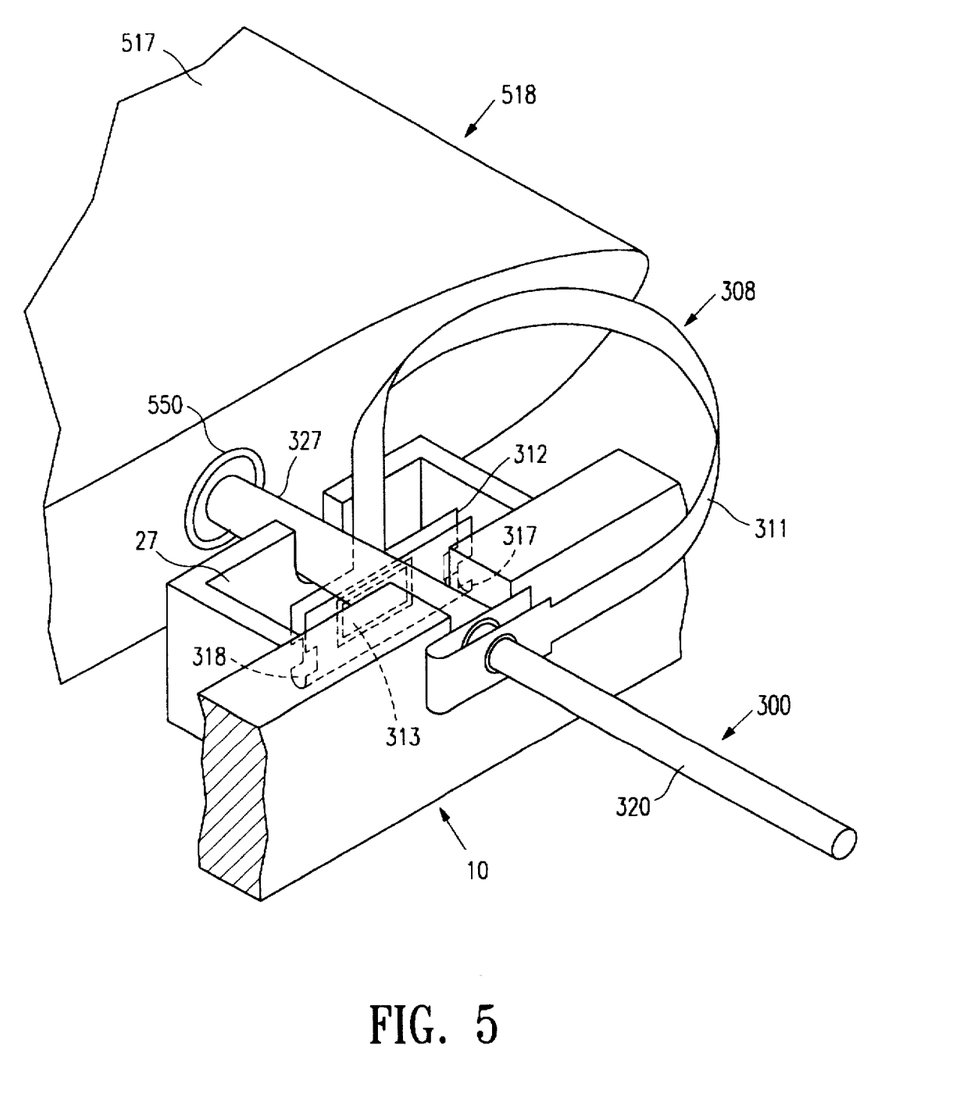
FIG. 5 illustrates the IV set adaptor connected to an infusion device.

FIG. 5 shows IV set adaptor 308 inserted within the containment means 27 of pump 10. First, a non-activating IV set 518 that includes a fluid reservoir 517 is positioned in the pump 10. Because the non-activating IV set 518 has no activator 29 for engaging the detector element in the containment means 27, the pump 10 is disabled. The CFS 300 of the IV set 518 has a connector 327, which is inserted into a CFS connector 550 on the fluid bag 517. The IV set adaptor 308, which may be coupled to the CFS 300, as shown, is then properly inserted and positioned within containment means 27. The adaptor 308 engages the detector element in the containment means 27. The pump 10 thereby detects the presence of an activating IV set equipped with activator 29. The adaptor 308 thus enables the pump 10 to be used with the non-activating IV set 518, despite the absence of an activating IV set.

OPERATION

Operation of pump 10 is now described with reference to FIGS. 1–5, it being further understood that the present operational description applies similarly to variations of the pump, with pump 10 being merely exemplary. Infusion of treatment fluid is performed in one instance by placing a prefilled treatment fluid bag 18 in the receptacle 16 after the cover 14 is removed from the base 12. The outlet tube 20 is fed through the opening 22.

The cover 14 is slid back onto the base 12. The tight fit of the bag 18 in the receptacle 16 impinges the bag 18 against a bladder (not shown) as the cover 14 is being positioned. This drives any residual drive fluid retained in the bladder out into the surrounding atmosphere via an outlet. The preferred drive fluid is ambient air. The latch 34 is then slid shut to lock the cover 14 in place and seal off the vent 38 from the atmosphere. The closing of the latch 34 can cooperate with a switch (not shown) to activate a drive fluid pump. In an alternate embodiment, the drive fluid pump can be activated by the operator through a command to input station 30.

When the pump 10 is activated, air is drawn through the port and is fed under pressure to the bladder. The pressurized air inflates the bladder within the confined receptacle 16 impinging both the bladder and bag 18 against the inner surfaces of the base 12 and cover 14. Once the treatment fluid bag 18 is pressurized, its contents can be purged of air (e.g., by opening the clamp and letting air out of the bag, then closing the clamp) and placed in communication with a desired vein of a patient using the site adaptor 24 at the end of tube 22.

The fluid bag 18 collapses at a rate proportional to the rate at which treatment fluid is expelled from the bag, thereby giving the bladder increasing amounts of space in which to expand. The bladder 68 can be inflated until it fills the entire volume of the confined receptacle 16, thereby completely collapsing the fluid bag 18 and expelling treatment fluid from it, and thereby delivering treatment fluid to the patient.

The flow rate of treatment fluid to the patient may be governed by the fixed cross-sectional area of the outlet tube 20 and the pumping pressure of the pump 10. A cross-sectional area of the tube 20 can be selected other than its area of manufacture by fixing the flow restrictor 326 on the tube 20 to reduce its cross-sectional area. Variable flow rate adjustment may also be achieved by means of a control assembly (not shown) acting as a feedback circuit.

The CFS 300 of the present invention limits the flow rate of fluid when the pump 10 is in a free-flow condition. Free-flow can occur, for example, if a malfunction occurs in the pump 10, resulting in treatment fluid being delivered to the patient at an uncontrolled rate. The CFS 300 limits the free-flow rate, such that fluid is delivered at a fraction of normal fluid delivery rate. This reduced free-flow rate should avert any possible medical problem that can occur if the patient receives fluid at the normal operating flow rate of the pump 10 when a free-flow condition exists.

The IV set adaptor 308 of the present invention permits use of non-activating IV sets in a pump configured to be used only with activating IV sets that have an activator 29. When a non-activating IV set 518 is positioned within the pump 10, the adaptor 308 is positioned within the contaminant means 27, which is fitted with a detector element. The adaptor 308 interacts with the detector element and enables the pump 10, even in the absence of the activator 29. As a result, non-activating IV sets 518 can be used with an activator-based pump.

The materials for construction of the pumps 10 and 40 are generally and preferably selected to be both inexpensive and lightweight. This enables the pump 10 to be portable and, if desired, disposable after each of one or several uses.

While the particular infusion pumps, CFS, and IV set adaptor as herein shown and disclosed in detail are fully capable of obtaining the objects and providing the advantages herein before stated, the disclosure is to be understood as merely illustrative of the presently preferred embodiments of the invention.

I claim:

1. A detachable apparatus for limiting the rate at which a fluid is supplied to a patient by a positive pressure infusion device, the infusion device having an operating device pressure of at least approximately 2 psi, the detachable apparatus comprising:

a constrained flow segment ("CFS"), coupleable to and detachable from the infusion device for delivering fluid to the patient from the infusion device, the CFS having a length in a range of about 28 to 38 inches, an inside diameter in a range of about 0.0025 to 0.05 of an inch, and a hydraulic resistance which is a function of the length and inside diameter; the CFS for (1) delivering fluid to the patient from the infusion device at a controlled flow rate determined by the operating device pressure and the hydraulic resistance of the CFS when the detachable apparatus is not in a free-flow condition, and (2) limiting a maximum flow rate of the detachable apparatus by the hydraulic resistance of the CFS to a range of approximately 7% to 16% of the controlled flow rate when the detachable apparatus is in a free-flow condition.

2. The apparatus of claim 1 wherein the CFS has a tubing segment having a length in a range of about 28 to 40 inches.

3. The apparatus of claim 2 wherein the inside diameter of the tubing segment is in a range of about 0.003 to 0.025 of an inch.

4. A detachable apparatus for limiting the rate at which a fluid is supplied to a patient by a positive pressure infusion device, the infusion device having an operating device pressure of at least approximately 2 psi, the detachable apparatus comprising:

a constrained flow segment ("CFS"), coupleable to and detachable from the infusion device, for delivering fluid to the patient from the infusion device, the CFS having a length in a range of about 28 to 38 inches, an inside diameter in a range of about 0.0025 to 0.05 of an inch, and a hydraulic resistance which is a function of the length and inside diameter; the CFS for (1) delivering fluid to the patient from the infusion device at a controlled flow rate determined by the operating device pressure and the hydraulic resistance of the CFS when the detachable apparatus is not in a free-flow condition, and (2) limiting a maximum flow rate of the detachable apparatus by the hydraulic resistance of the CFS to a range of approximately 30% to 60% of the controlled flow rate when the detachable apparatus is in a free-flow condition.

5. The apparatus of claim 4 wherein the CFS has a tubing segment having a length in a range of about 60 to 76 inches.

6. The apparatus of claim 5 wherein the inside diameter of the tubing segment is in a range of about 0.004 to 0.035 of an inch.

7. A detachable apparatus for limiting the rate at which a fluid is supplied to a patient by a positive pressure infusion device, the infusion device having an operating device pressure of at least approximately 2 psi, the detachable apparatus comprising:

a constrained flow segment ("CFS"), coupleable to and detachable from the infusion device, for delivering fluid to the patient from the infusion device, the CFS having a length in a range of about 28 to 38 inches, an inside diameter in a range of about 0.0025 to 0.05 of an inch, and a hydraulic resistance which is a function of the length and inside diameter; the CFS for (1) delivering fluid to the patient from the infusion device at a controlled flow rate determined by the operating device pressure and the hydraulic resistance of the CFS when the detachable apparatus is not in a free-flow condition, and (2) limiting a maximum flow rate of the detachable apparatus by the hydraulic resistance of the CFS to a range of approximately 16% to 30% of the controlled flow rate when the detachable apparatus is in a free-flow condition.

8. The apparatus of claim 7 wherein the CFS has a tubing segment having a length in a range of about 60 to 76 inches.

9. The apparatus of claim 8 wherein the inside diameter of the tubing segment is in a range of about 0.003 to 0.03 of an inch.

10. A method for limiting the rate at which fluid is supplied to a patient by a positive pressure infusion device, the method comprising the steps of:

(a) coupling a detachable constrained flow segment ("CFS") to a positive pressure infusion device having an operating device pressure of at least approximately 2 psi the CFS having a length, an inside diameter, and a hydraulic resistance which is a function of the length and the inside diameter;

(b) delivering fluid to the patient at a controlled rate determined by the operating device pressure and the hydraulic resistance of the CFS when the infusion device is in a non-free-flow condition; and (C) limiting a maximum flow rate of the CFS to less than about 50% of the controlled flow rate when the CFS is in a free-flow condition.

11. The method of claim 10, wherein the CFS has a tubing segment, the method further comprising the steps of:

(a) selecting the length of the tubing segment to be in a range of about 28 to 80 inches;

(b) selecting the inside diameter of the tubing segment to be in a range of about 0.0025 to 0.05 of an inch; and (c) selecting the operating device pressure to be in a range of approximately 4.5 to 13 psi.

12. The method of claim 11, further comprising selecting the operating device pressure to be in a range of about 5 to 8 psi and the maximum flow rate of the CFS in a free-flow condition to be in a range of approximately 13% to 30% of the controlled flow rate.

13. The method of claim 11, further comprising selecting the operating device pressure to be in a range of about 9 to 12 psi and the maximum flow rate of the CFS in a free-flow condition to be in a range of approximately 7% to 16% of the controlled flow rate.

14. The method of claim 11, further comprising selecting the operating device pressure to be in a range of about 5 to 8 psi and the maximum flow rate of the CFS in a free-flow condition to be in a range of approximately 30% to 50% of the controlled flow rate.

15. The method of claim 11, further comprising selecting the operating device pressure to be in a range of about 9 to 12 psi and the maximum flow rate of the CFS in a free-flow condition to be in a range of approximately 16% to 30% of the controlled flow rate.

16. An adaptor for enabling a non-activating intravascular set ("IV set") to be used with an infusion device, where the infusion device is configured for use with an activating IV set, the infusion device having a detector element for detecting whether an activating IV set is being used with the infusion device, the infusion device being activated in response to detection of an activating IV set such that the infusion device is disabled if the detector element fails to detect an activating IV set, the adaptor comprising:

an active element, independent of the non-activating IV set, for interacting with the detector element and causing the detector element to detect the presence of an activating IV set when the non-activating IV set is being used with the infusion device.

17. The adaptor of claim 16, further comprising:

(a) holder means for holding the active element and for facilitating interaction between the active element and the detector element.

18. The adaptor of claim 17 wherein the holder means has an extension end and a detector end, the extension end being coupled to a constrained flow segment of the non-activating IV set and the detector end being for engaging the detector element.

19. The adaptor of claim 18 wherein the detector end of the holder means has a first portion and a second portion, the first portion having a recess for accepting the active element and the second portion covering the recess.

20. The adaptor of claim 19, further comprising an adhesive for bonding the first portion to the second portion.

21. The adaptor of claim 16 wherein the active element comprises means for magnetically activating the infusion device.

22. The adaptor of claim 21 wherein the active element comprises a metallic object for activating a magnetic switch of the infusion device.

23. The adaptor of claim 16, further comprising a reflective surface for reflecting a wave radiated by the detector back to the detector.

24. The adaptor of claim 16 wherein the active element comprises means for completing an electric circuit of the detector.

25. A system for enabling an infusion device to be used with a non-activating intravascular set ("IV set"), where the infusion device is configured for use with an activating IV set, the system comprising:

(a) a detector, coupled to the infusion device, for detecting whether an activating IV set is being used with the infusion device, whereby the infusion device is disabled if the detector fails to detect the presence of an activating IV set; and (b) an adaptor for enabling the infusion detector to be used with the non-activating IV set, the adaptor including an active element, independent of the non-activating IV set, for indicating to the detector the presence of an activating IV set when the non-activating IV set is actually being used with the infusion pump.

26. The system of claim 25 wherein the adaptor further includes holder means having a first portion with a recess for holding the active element and a second portion for covering the recess and active element.

27. The system of claim 25 wherein the adaptor further includes holder means for holding the active element and engaging the detector, the holder means having at least one tab for securing the holder means to the detector.

28. The system of claim 25, the system further comprising a coupler for coupling the active element to the non-activating IV set.

29. An adaptor for enabling a non-activating intravenous set ("IV set") to be used with an infusion device, where the infusion device is configured for use with an activating IV set, the activating IV set having a constrained flow segment ("CFS") and the infusion device having a detector for detecting whether an activating IV set is being used with the infusion device, such that the infusion device is disabled if the detector fails to detect the presence of an activating IV set, the adaptor comprising:

(a) a holder; and (b) an active element, held by the holder, for indicating to the detector that an activating IV set is present and thereby activating the infusion device when the non-activating IV set is being used with the infusion device and when the holder is placed relative to the infusion device in a manner that allows interaction between the active element and the detector.

30. The adaptor of claim 29 wherein the active element comprises an electronic element.

31. The adaptor of claim 29 wherein the active element comprises a magnetic element.

32. A method for enabling a non-activating intravascular set ("IV set") to be used with an infusion device, where the infusion device is configured for use with an activating IV set, the infusion device having a detector for detecting whether an activating IV set is being used with the infusion device, such that the infusion device is disabled if the detector fails to detect the presence of an activating IV set, the method comprising the steps of:

(a) placing a non-activating IV set in the infusion device;

(b) positioning an active element relative to the detector;

(c) detecting the presence of the activating IV set by the detector in response to step (b); and (d) enabling the infusion device in response to step (c).

* * * * *